United States Patent [19]

Brodin et al.

[11] Patent Number: 5,086,053
[45] Date of Patent: Feb. 4, 1992

[54] DERIVATIVES OF 1,3,4-THIADIAZOLE, A METHOD OF OBTAINING THEM AND PHARMACEUTICAL COMPOSITIONS CONTAINING THEM

[75] Inventors: Roger Brodin; Dominique Olliero, both of Montpellier; Paul Worms, St. Gely Du Fesc, all of France

[73] Assignee: Sanofi, Paris, France

[21] Appl. No.: 394,321

[22] Filed: Aug. 16, 1989

[30] Foreign Application Priority Data

Aug. 25, 1988 [FR] France .................... 88 11226

[51] Int. Cl.$^5$ ............ C07D 285/135; C07D 417/12; A61K 31/41
[52] U.S. Cl. ................. 514/236.2; 514/255; 514/326; 514/342; 514/363; 514/134; 514/367; 546/209; 546/277; 548/138
[58] Field of Search ............ 548/138; 514/363, 236.2, 514/255, 326, 342; 546/277, 209; 544/134, 367

[56] References Cited

U.S. PATENT DOCUMENTS 4,596,802 6/1980 Wermuth .................. 544/134

OTHER PUBLICATIONS

Lalezari, J. Pharm. Sci., 64, 1250 (1975).

Primary Examiner—Robert Gerstl
Attorney, Agent, or Firm—Foley & Lardner

[57] ABSTRACT

The present invention relates to thiadiazole derivatives having the formula:

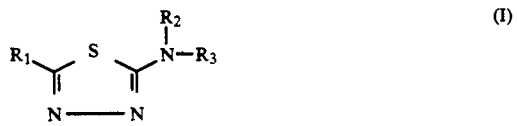

in which:
- $R_1$ represents a phenyl group, non-substituted or substitued 1 to 3 times by a halogen atom, preferably chlorine or fluorine, or by a $C_1$-$C_4$ alkyl group, preferably the methyl group, or by a $C_1$-$C_4$ alkoxy group, preferably the methoxy group, or by a hydroxy group or by a trifluoromethyl group or a phenyl group substituted simultaneously by 1 to 3 halogen atoms and by 1 or 2 methyl groupings;
- $R_2$ represents hydrogen or a $C_1$-$C_4$ alkyl group,
- $R_3$ represents an alkylamino group or a heterocyclic group, Application: Drugs for treatment of notably senile dementia.

14 Claims, No Drawings

DERIVATIVES OF 1,3,4-THIADIAZOLE, A METHOD OF OBTAINING THEM AND PHARMACEUTICAL COMPOSITIONS CONTAINING THEM

The invention relates to novel thiadiazole derivatives, the method of preparing them, and the use thereof in therapy.

Some thiadiazole derivatives are known in the prior art. European patent application 183 577 describes derivatives of 2-(2-morpholino ethylamino) thiadiazole having the formula:

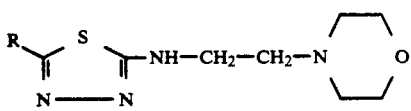

in which R represents an alkyl or cycloalkyl or biphenyl or naphthyl or phenyl group (substituted if required).

These compounds have antidepressant and dopaminomimetic properties.

Also an article in the Journal of Pharmaceutical Sciences, 1975, 65, No. 7, 1250-1252 describes derivatives of 2-amino thiadiazole having the formulae:

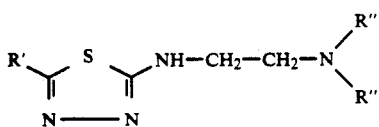

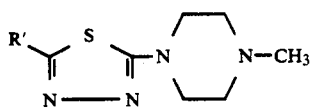

in which:
R' represents methyl, trifluoromethyl or monosubstituted phenyl and
R" represents methyl or ethyl.

These compounds have antihistamine and anticholinergic properties.

Accordingly, European patent application 183 577 and the aforementioned article from J. Pharm. Sci. describe 1,3,4-thiadiazole derivatives substituted by a phenyl grouping in position 5 and by an amine grouping in position 2.

In both cases the amine grouping has the form:

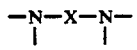

in which X is a straight-chain carbon group or included in a ring system comprising two carbon atoms.

In the invention, we have found novel 1,3,4-thiadiazole derivatives carrying a phenyl grouping, substituted if required, in position 5 and an amine grouping having the form

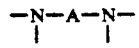

in position 2, where the grouping A between the two nitrogen atoms comprises three or four carbon atoms, the grouping being either straight-chain, i.e. trimethylene or tetramethylene, or included in a ring containing either of the nitrogen atoms.

In completely surprising manner, it has been found that these compounds are agonists of the cholinergic muscarinic system whereas on the contrary the prior-art compounds where the grouping X contains only two carbon atoms have no effect on the cholinergic muscarinic system.

According to a first feature, the invention relates, as novel products, to thiadiazole derivatives having the general formula:

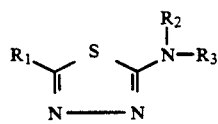

in which:

$R_1$ represents a phenyl group, non-substituted or substitued 1 to 3 times by a halogen atom, preferably chlorine or fluorine, or by a $C_1$-$C_4$ alkyl group, preferably the methyl group, or by a $C_1$-$C_4$ alkoxy group, preferably the methoxy group, or by a hydroxy group or by a trifluoromethyl group or a phenyl group substituted simultaneously by 1 to 3 halogen atoms and by 1 or 2 methyl groupings;

$R_2$ represents hydrogen or a $C_1$-$C_4$ alkyl group, $R_3$ represents:

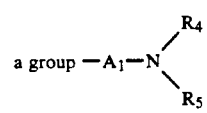

in which $A_1$ denotes a straight chain $C_3$-$C_4$ alkyl group, $R_4$ and $R_5$ considered independently represent hydrogen or a $C_1$-$C_4$ alkyl group, or $R_4$ and $R_5$ considered with the nitrogen atom bonded thereto constitute a heterocyclic ring system made up of 5 or 6 links and if required containing a second heteroatom, inter alia one of the following rings: pyrrolidine, imidazole, piperidine, morpholine, piperazine or N-alkylpiperazine; or

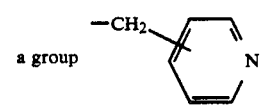

where the methylene group substitutes the pyridine ring in position 3 or 4;

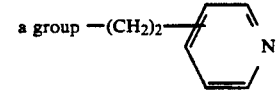

where the ethylene group substitutes the pyridine ring in position 2 or 3;

a group —$(CH_2)_p$— 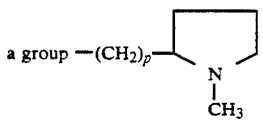

with p = 2 or 3;

a group —$A_2$ 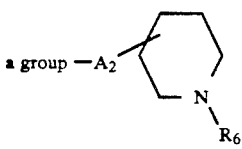

where $R_6$ denotes a methyl or ethyl group and $A_2$ denotes a $(CH_2)_m$ group where m = 1 or 2, the $A_2$ group being in position 3 or 4 of the piperidine ring when m = 1 and in position 2 or 3 thereof when m = 2, a group 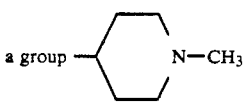

or alternatively the substituent $$\begin{array}{c} R_2 \\ | \\ -N-R_3 \end{array}$$

represents a group

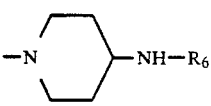

where $R_6$ is as indicated hereinbefore and salts of addition thereof with mineral or organic acids.

The invention also relates to a method of obtaining compounds of formula (I), the method being characterized in that a corresponding 2-halogeno 1,3,4-thiadiazole having the formula:

 (II)

in which X represents chlorine or bromine and $R_1$ is as above defined is reacted with a compound having the formula:

—HN $R'_2R'_3$ (III)

in which $R'_2$ and $R'_3$ have the same meanings as $R_2$ and $R_3$ defined hereinbefore $R'_2$ is a protective group when hydrogen and, if required, the product thus obtained is converted into one of its pharmaceutically acceptable salts.

the substitution reaction (II)+(III) is brought about in the presence either of a reagent which fixes the hydracid XH formed during the reaction, or an excess of amine (III) at a temperature between 40° C. and 130° C. The reaction is carried out in a polar solvent such as alkanol e.g. ethanol, n-butanol or isopropanol or in a non-polar solvent such as benzene. It is preferable to operate in a nitrogen atmosphere to avoid carbonation of the amine (I) formed.

The resulting product is isolated by conventional methods, e.g. by evaporating the solvent and chromotographing the residue, or by evaporating the solvent and isolating the base, after recrystallization if required, or by evaporating the solvent and isolating the product in the form of one of its salts by treating the residue, consisting of the crude free base, with a solution of an acid, e.g. in an alcohol.

When the final product is isolated in salt form, the free base can be released by neutralization.

When $R_1$ denotes the hydroxyphenyl or polyhydroxyphenyl group, the compounds according to the invention are obtained by demethylation of compounds (I) in which $R_1$ represents a methoxyphenyl or polymethoxyphenyl group, using a known method, e.g. heating in an acid medium.

The halogenated starting products (II) are known or can be prepared by known methods. For example, products (II) can be obtained from the following amino compounds:

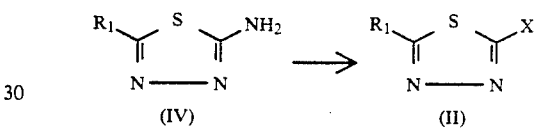

Diazotation is carried out, followed by decomposition of the diazonium salt, in the presence of hydracid XH, by the methods described in Chemische Berichte, 1956, 89, 1534–1543 and Tetrahedron, 1968, 24 3209–3217.

Amino thiadiazoles (IV) are known or can be prepared by known methods, consisting in converting the acid $R_1$COOH or the acid chloride $R_1$OCL into the corresponding thiosemicarbazide and in conversion thereof to cyclic form, using a dehydration agent by the methods described in J. Pharm. Soc. Japan, 1952, 72, 373–375; J. Chem. Soc., 1949, 1163–1167 and Can. J. Chem., 1959, 37, 1121–1123. The dehydration agent can be polyphosphoric acid or methane sulphonic acid or sulphuric acid when $R_1$ represents a phenyl grouping.

Compounds HN $R_2 R_3$ (III) are known or are prepared by known methods.

When $R_3$ represents a group $A_1$—$NR_4 R_5$ in which $A_1$ is tetramethylene, either the diamine $R_2NH$—$(CH_2)_4$—$N R_4 R_5$ (III)

can be prepared by known methods, or it can be reacted with the thiadiazole derivative (II) or the compound (I) according to the invention can be obtained by catalytic hydrogenation of the corresponding acetylene derivative of thiadiazole (V), in accordance with the following reaction diagram:

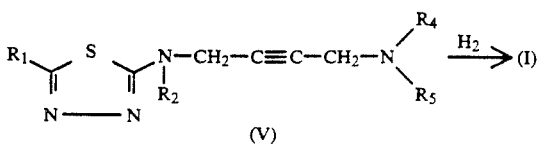

Compound (V) can be obtained by substitution of thiadiazole (II) by 2-butyne 1,4-diamine (VI):

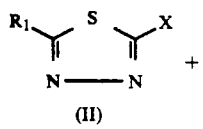
+
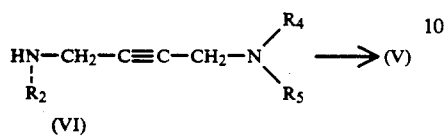 ⟶ (V)

The reaction is carried out under conditions similar to those described for substitution of (II) by the derivative HN $R_2 R_3$ (III).

Compounds (VI) can be prepared by various known methods depending on the values of the substituents $R_2$, $R_4$ and $R_5$.

For example, a symmetrical compound (VI) in which $R_2=R_4=$alkyl and $R_5=H$ is prepared from 2-butyne 1,4-diol by action of excess thionyl chloride in pyridine followed by action of the amine $NH_2R_2$ on the resulting dichlorinated derivative, in accordance with the following reaction diagram described in J. Chem. Soc., 1946, 1007-1014:

Also, derivatives (VI) in which $R_2$ represents hydrogen can be synthesized form N-propargyl phthalimide, which is subjected to a Mannich reaction to form the N(4-amino 2-butynyl) phthalimide by the method described in Eur. J. Med. Chem.—Chim. Ther., 1982, 17, 85-88.

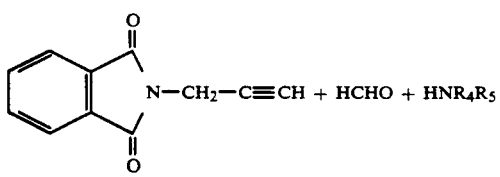

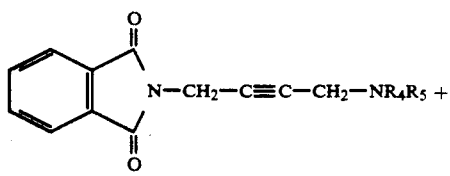

Finally, derivatives (VI) in which $R_2$ represents an alkyl can alternatively be synthesized by the methods described in Can. J. Chem., 1980, 58, 2183-2188; by aminomethylation of an N-alkyl N-propargylphosphoramide followed by acid hydrolysis of the product obtained, in accordance with the following reaction diagram:

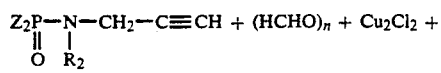

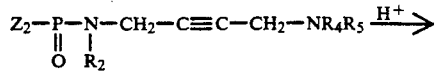

Z = alkyl

In the special case where $R_3$ represents a group:

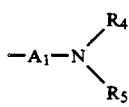

in which at least one of the substituents $R_4$ and $R_5$ is hydrogen, the amino derivatives (III) must be protected. They can be prepared from the aminonitrile $R_4NH-A'_1-CN$. This substance, when reacted with the anhydride $(Boc)_2O$, leads to the aminonitrile Boc—N—A'$_1$—CN
       |
       R$_4$ which, by reduction leads to the corresponding primary amine

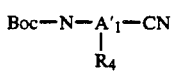 (VII)

where A'$_1$, deprived of a methylene group and Boc represent the tertiobutyloxycarbonyl grouping.

When $R_2$ is different from H, a known method is then used to prepare the appropriate diamine:

 (VIII)

The substitution reaction of thiadiazole (II) with diamine (VII) or (VIII) is carried out under the usual conditions. Finally, the resulting compound is deprotected in an acid medium to prepare the compound (I) according to the invention.

The following examples illustrate the invention without limiting it. In these examples, the term Boc denotes the tertiobutyloxycarbonyl grouping.

EXAMPLE 1

2-(3-dimethylamino propylamino)-5-(2,4,6-trimethylphenyl)-1,3,4 thiadiazole dihydrochloride: SR 45 341 A A) 2,4,6-trimethyl benzoyl thiosemicarbazide 37.25 g of thiosemicarbazide was dissolved in 400 ml dimethylformamide and 32.05 g of pyridine, after which 74 g of 2,4,6-trimethylbenzoyl chloride was added at 0° C. in 20 minutes. The reaction mixture was heated at 80°

C. for 2 hours and then concentrated to three-quarters in vacuo and the remaining mixture was poured into 1500 ml of cold water. The resulting white precipitate was filtered, washed in water and dried.

78 g was obtained
Yield: 81%
Melting-point above 260° C.

B) 2-amino 5-(2,4,6-trimethylphenyl)-1,3,4-thiadiazole 60 g of 2,4,6-trimethylbenzoyl thiosemicarbazide previously obtained was mixed with 1250 g of polyphosphoric acid. The mixture was heated at 130° C. with agitation for 18 hours, then poured into 20 liters of cold water. The resulting precipitate was filtered, washed in ethyl acetate and in isopropyl ether and dried.

Weight obtained: 22.9 g
Yield: 41%
Melting-point: about 280° C.

C) 2-chloro 6-(2,4,6-trimethylphenyl)-1,3,4-thiadiazole 24.5 g of 2-amino 5-(2,4,6-trimethylphenyl) 1,3,4-thiadiazole and 122.5 g of sodium nitrite were mixed in a mortar. The mixture was added in portions at −10° C. and for two and a half hours to a solution containing 302 ml of hydrochloric acid concentrated to 37% (d=1.19) and 5 g copper. Next, the reaction mixture was slowly heated to 0° C. after 30 minutes and +15° C. after an hour. The mixture was left overnight at ambient temperature, then 1 liter of water was added. It was extracted twice with 700 ml of ethylacetate, and then washed with 500 ml of 2-N soda and 200 ml of water saturated with sodium chloride. It was dried over sodium sulphate, concentrated and the residue was chromatographed on silica gel. The impurities at the top were eliminated by a mixture of methylene chloride and hexane (60/40), after which the expected product was eluted with methylene chloride.

Weight obtained: 17.3 g
Melting-point: 90-92° C.
Yield: 65%

D) SR 45 341 A 3.6 g of dimethylamino propylamine was added to 2.8 g of 2-chloro 5-(2,4,6-trimethylphenyl) 1,3,4-thiadiazole dissolved in 60 ml butanol and reflux-heated in a nitrogen atmosphere for 18 hours. The mixture was concentrated then dissolved in 200 ml ethyl acetate and extracted with twice 50 ml of 4 N hydrochloric acid. The medium was made basic by adding concentrated soda and cooling in ice, then extracted with twice 150 of ethyl acetate, dried on sodium sulphate and concentrated. After chromatography on alumina, using ethyl acetate as an eluent, the impurities at the top were eliminated and the expected product was eluted in base form by a mixture of ethyl acetate and methanol (50/50).

Weight obtained: 2.7 g
Melting-point: 102°-104° C.
Yield: 76%

The mixture was dissolved in 150 ml ethanol and 2.26 ml of concentrated hydrochloric acid was added. The mixture was left to crystallize and then filtered to obtain the expected product.

Weight obtained: 2.9 g
Yield: 65%
Melting-point: 216-218° C.

EXAMPLE 2

2-(3-dimethylamino propylamino) 5-(3,5-dibromo-2,4,6-trimethylphenyl) 1,3,4-thiadiazole: SR 45 639 A A) 2-bromo 5-(5-bromo-2,4,6-trimethylphenyl)-1,3,4-thiadiazole and 2-bromo 5-(3,5-dibromo-2,4,6-trimethylphenyl)-1,3,4-tiadiazole 24.5 g of 2-amino 5-(2,4,6-trimethylphenyl) thiadiazole obtained previously was mixed with 122.5 g of sodium nitride in a mortar. The composition was added in portions at −30° C. to a solution comprising 402 ml of 47% hydrobromic acid and 5 g copper. The mixture was slowly and gradually heated to a temperature of −20° C. after 1 hour and +10° C. after 2 hours, then heated to 35° C. for 2 hours. 1 liter of cold water is added, followed by extraction twice with 700 ml of ethylacetate. The mixture was washed with 500 ml of 2 N soda then with 200 ml of water saturated with sodium chloride. It was dried on sodium sulphate and concentrated. The residue was chromatographed on silica gel and eluted with methylene chloride.

The first eluted compound was 2-bromo 5-(3,5-dibromo-2,4,6-trimethylphenyl)-1,3,4-thiadiazole.

Weight obtained: 6.2 g
Melting-point: 131-132° C.

the second eluted compound was 2-bromo 5-(5-bromo-2,4,6-trimethylphenyl)-1,3,4-thiadiazole.

Weight obtained: 19.3 g
Melting-point: 91° C.

B) SR 45 639 A a solution of 2.2 g of the dibromo derivative and 2.04 g of dimethylamino propylamine was reflux-heated with agitation and in a nitrogen atmosphere overnight in 20 ml of n-butanol. The mixture was concentrated then dissolved in 200 ml of ethyl acetate. It was extracted twice with 100 ml of 4 N hydrochloric acid. It was decanted then washed with 50 ml ethyl acetate. The mixture was made alkaline by adding 120 ml of concentrated soda and cooling. It was extracted with ethylacetate and then dried on sodium sulphate and concentrated. 1.9 g of the expected product was obtained in base form.

Yield: 82%
Melting-point: 162-164° C.

The base was dissolved in 200 ml of absolute alcohol, 1.6 ml of concentrated hydrochloric acid was added, and the mixture was filtered while hot, concentrated to 100 ml. crystallized and then centrifuge-dried.

1.8 g of the expected product was obtained.
Melting-point: 234-236° C.
Yield: 65%

EXAMPLE 3

Dihydrochloride of 2-(4-diethylamino butylamino)-5-phenyl-1,3,4-thiadiazole: SR 45 339 A A) 2-[(4-diethylamino butyn-2-yl) amino]-5-phenyl-1,3,4-thiadiazole hydrate 4 g of 2-bromo 5-phenyl-1,3,4-thiadiazole prepared as indicated in Tetrahedron, 1968, 24, 3214 was mixed with 6.98 g of 4-diethylamino butyn-2-yl amine prepared as indicated in Eur. J. Med. Chem. Chim. Ther., 1982, 17, 85-88. The mixture was reflux-heated in 100 ml of ethanol for 48 hours. The ethanol was concentrated in vacuo, and the residue was dissolved in a 4 N soda solution. It was extracted with ethyl acetate, then the organic phase was washed with water, dried on sodium sulphate and the residual oil was chromatographed on silica gel, using ethylacetate as the eluent.

The pure fractions were concentrated in vacuo. Recrystallization from a mixture of hexane and isopropyl ether (50/50).

The product crystallized with 1 molecule of water.
Weight: 0.26 g
Melting-point: 55° C.

B) SR 45 339 A

Hydrogenation at atmospheric pressure was carried out for 20 hours on 1.75 g of the compound prepared in the previous step and dissolved in 100 ml ethanol and 1 ml of concentrated hydrochloric acid, in the presence of platinum prepared in situ from 0.34 g of platinum oxide.

The mixture was flushed out with nitrogen and the catalyst was filtered. The filtrate was concentrated, dissolved in ethyl acetate, and extracted with twice 50 ml of 4 N hydrochloric acid. Dilute soda was added to obtain a basic pH (pH=10-11). The mixture was extracted with ethylacetate, dried and concentrated.

Weight obtained: 1.4 g
Yield: 80%

The base was dissolved in 70 ml ethanol and, after adding 1.1 of concentrated hydrochloric acid, was left to crystallize. It was centrifuge-dried then washed in isopropyl ether.

Weight obtained: 0.85 g
Total yield: 39%
Melting-point: 158-160° C.

EXAMPLE 4

2-(4-dimethylamino butylamino)-5-(2,4,6-trimethylphenyl)-1,3,4-thiadiazole dihydrochloride: SR 45 641 A 4-dimethylamino butylamine was prepared by the method reported in Beilstein, Volume 4, Supplement 3, 573-574.

4.28 g of 4-dimethylamino butylamine and 2.2 g 2-chloro-5-(2,4,6-trimethylphenyl)-thiadiazole prepared as in Example 1, stage C, was added to 60 ml of normal butanol.

The mixture was refluxed in a nitrogen atmosphere for 1 week, after which 2.14 g of 4-dimethylamino butylamine was added and heating was continued for 1 week. After the mixture has been concentrated, the residue was dissolved in ethyl acetate, extracted twice with 50 ml of 4 N hydrochloric acid, then washed with ethyl acetate. The mixture was made alkaline with concentrated soda and cooled, then extracted with ethyl acetate, dried on sodium sulphate and concentrated. The residue was chromatographed on alumina; the impurities at the top were eliminated by elution with ethyl acetate, after which the expected product was eluted with a mixture of ethyl acetate and methanol (80/20). After concentration, an oil formed and coagulated and the expected product was obtained in base form.

Weight obtained: 1.25 g
Yield: 39%

The product was dissolve din 100 ml of absolute alcohol, 10 ml of concentrated hydrochloric acid was added and the mixture was filtered while hot to remove impurities, then concentrated to a volume of 30 ml left to crystallize and then centrifuge-dried to obtain the expected salt.

Weight: 0.8 g
Melting-point: 216-218° C.
Total yield: 22%

EXAMPLE 5

2-(3-methylamino propylamino) 5-(2,4,6-trimethylphenyl) 1,3,4-thiadiazole dihydrochloride: SR 45 418 A

A) N-phenyl N-Boc 3-amino propylamine 34 g of N-3-methylamino-propionitrile was poured into 100 ml dichloromethane. 88 g of (Boc)$_2$O was added with agitation and left for 18 hours with agitation at ambient temperature. The product after concentration was 77 g of N-methyl N-Boc 3-amino propionitrile, which was used as such.

The product obtained was mixed with 800 ml water, 400 ml ethanol and 80 ml ammonia, followed by catalytic hydrogenation on activated Raney nickel for 10 minutes. The volume of hydrogen absorbed was 16.7 liters. The mixture was concentrated, then dissolved in methylene chloride, decanted, dried on sodium sulphate and calcium chloride, and concentrated. An oil was obtained and used as such in the next step.

B) SR 45 418 A

A mixture containing 2.2 g of 2-chloro 5-(2,4,6-trimethylphenyl 1,3,4-thiadiazole and 8.67 g of N-methyl N-Boc 3-amino propylamine was reflux-heated for 72 hours under nitrogen and with agitation in 60 ml of normal butanol. The mixture was concentrated then dissolved in 200 ml water and extracted twice with 200 ml of methylene chloride. It was washed in water, dried on sodium sulphate and concentrated. It was chromatographed on silica gel. The expected product was eluted with ethyl acetate. After concentration the residual oil crystallized form isopropyl ether. The product was in the form of a base in which the terminal nitrogen carried a Boc grouping. The substance was 2-(N-methyl N-Boc 3-amino propylamino) 5-(2,4,6-trimethylphenyl)-1,3,4-thiadiazole.

Weight obtained: 2.2 g
Melting-point: 113-115° C.
Yield: 65%

The base was dissolved in 150 ml of absolute alcohol followed by addition of 2.9 ml of concentrated hydrochloric acid. The mixture was concentrated to a volume of 100 ml, left to crystallize and filtered. 1.8 g of the expected product was obtained.

Melting-point: 256-258° C.
Total yield: 54%

EXAMPLE 6

2-(4-methylamino piperidino)-5-phenyl-1,3,4-thiadiazole dihydrochloride: SR 44 825 A 2.4 g of 2-bromo 5-phenyl-1,3,4-thiadiazole was dissolved in 25 ml of normal butanol, 3.85 g of 4methylamino-1-methyl-piperidine were added and the mixture was reflux-heated in a nitrogen atmosphere. It was cooled, the precipitate was filtered and the filtrate was concentrated in vacuo. The residue was dissolve din 100 ml of ethyl acetate then extracted twice with 50 ml of 3 N hydrochloric acid. It was made alkaline with 50 ml of concentrated soda with cooling. It was extracted with twice 100 ml of ethyl acetate, dried on sodium sulphate and concentrated. The residue was recrystallized form a mixture of methylene chloride and isopropyl ether. The product described was obtained in the form of a base.
Weight: 0.83 g
Melting-point: 96° C.
Yield: 29%

The base was dissolved in 50 ml of absolute ethanol. 0.74 ml of concentrated hydrochloric acid were added, filtered when hot then concentrated to three-quarters on a water bath and left to crystallize.
Weight: 0.9 g
Total yield: 25%
Melting-point >260° C.

The RMN spectrum of SR 44 825 A was recorded in the DMSO at 250 MHz.

In order to interpret the spectrum, the following abbreviations have been used:

D=doublet, T=triplet, Q=quartet, M=multiplet, J≦coupling constant, a=axial, e=equatorial.

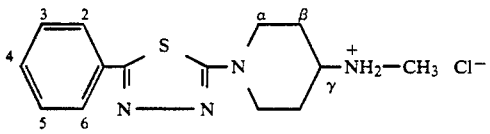

| RMN SPECTRUM | | | |
|---|---|---|---|
| Delta | Aspect | Protons | Attribution |
| 1,7 | Q D<br>J = 4Hz<br>J = 14Hz | 2 H | Hβa |
| 2,15 | D of Q<br>J = 4Hz<br>J = 14Hz | 2 H | Hβe |
| 2,5 | T | 3 H | CH₃ |
| 3,25 | T of D<br>J = 14Hz<br>J = 4Hz | 2 H | Hαa |
| 4 | D of T<br>J = 14Hz<br>J = 4Hz | 2 H | Hαe |
| 7,5 | M | 3 H | H 3,4 and 5 |
| 7,75 | M | 2 H | H 2 and 6 |

EXAMPLE 7

Dihydrochloride and hydrate of 2-[N-methyl N-(1-methyl 4-piperidyl) amino -5-phenyl-1,3,4-thiadiazole: SR 44828 A 2.4 g of 2-bromo 5-phenyl-1,3,4-thiadiazole was dissolved in 25 ml of normal butanol. 3.85 g of 4-methylamino-1-methyl-piperidine were added and reflux-heated overnight in a nitrogen atmosphere. The mixture was cooled, the resulting precipitate was filtered and dissolved in 20 ml of 2 N soda. The mixture was extracted with 100 ml of methylene chloride, dried on sodium sulphate and concentrated, followed by chromatography on silica gel and eluting with a mixture of methylene chloride and methanol (60/40).

0.77 g of the expected product was obtained in base form.
Melting-point: 74°-76° C.
Yield: 27%

The base was dissolved in 50 ml of absolute ethanol, 0.62 ml of concentrate hydrochloric acid was added, insoluble substance was filtered when hot and concentrated to three-quarters in the water bath and left to crystallize.

Weight obtained: 0.65 g
Yield: 19%
Melting-point: 276°-278° C.

EXAMPLE 8

Dihydrochloride and hydrate of (4-pyridyl)-2-methylamino 5-(2,4,6-trimethylphenyl) 1,3,4-thiadiazole: SR 45 638 A 2.2 g of 2-chloro 5-(2,4,6-trimethylphenyl)-1,3,4-thiadiazole and 4.98 g of 4-aminomethyl-pyridine were mixed in 20 ml of normal butanol. The mixture was reflux-heated for 48 hours in a nitrogen atmosphere. The reaction mixture was concentrated then dissolved in 30 ml water and extracted twice with 50 ml of methylene chloride, dried on sodium sulphate and concentrated. The residue was chromatographed on alumina nd eluted with ethyl acetate. After the impurities of the first fraction had been eliminated, the subsequent fractions were concentrated and the residual oil was crystallized.

1.6 g of the expected product was obtained in base form.
Melting-point: 136°-138° C.
Yield: 56%

The base was dissolve din 100 ml of absolute ethanol and 1.3 ml of concentrated hydrochloric acid was added. The insoluble substance was filtered and the filtrate was concentrated to a total volume of 30 ml. It was left to crystallize, then centrifuge-dried to obtain the expected product.
Weight: 1.5 g
Melting-point: 200–202°C.
Total yield: 41%

EXAMPLE 9

2-(3-dimethylamino propylamino)-5-(3,4-dimethoxyphenyl)-1,3,4-thiadiazole dihydrochloride: SR 45 642 A A mixture comprising 4 g of 2-chloro-5-(3,4-dimethoxyphenyl)-1,3,4-thiadiazole and 6.36 g of 3-dimethylamino propylene was reflux-heated overnight in 30 ml normal butanol in a nitrogen atmosphere. The mixture was concentrated then dissolve din 100 ml ethyl acetate and extracted twice with 70 ml of 4 N hydrochloric acid. 90 ml of concentrated soda was added with cooling, and the resulting precipitate was filtered and washed with water. The precipitate was dissolved in methylene chloride, then dried on sodium sulphate and concentrated.

The extracted product was obtained in base form.
Weight: 4 g
Yield: 80%
Melting-point 147°-149° C.

2.25 g of the base was dissolved in 100 ml absolute ethanol and 1.787 ml of concentrated hydrochloric acid was added. The impurities were filtered when hot The filtrate was concentrated to a volume of 30 ml, then left to crystallize and filtered to obtain the expected salt.
Weight: 2.4 g
Melting-point: 210°-212° C.
Yield: 66%

EXAMPLE 10

Dihydrobromide, hydrate of 2-(dimethyl-3-amino propylamino)-5-(3,4-dihydroxyphenyl) 1,3,4-thiadazole: SR 45 643 A

A mixture containing 1.7 g of SR 45 642 in base form and 25 ml of 47% hydrobromic acid was reflux-heated for 7 hours. The mixture was concentrated in vacuo and then dissolved in 150 ml of hot absolute ethanol. It was filtered then concentrated to a volume of 50 ml. It was left to crystallize then filtered to obtain the expected product.

Weight: 2.45 g
Yield: 95%
Melting-point: 172°–174° C.

EXAMPLE 11

2-[(N-methyl 3-piperidyl) methylamino]-5-(4-chlorophenyl)-1,3,4-thiadiazole dihydrochloride: SR 45 491

A) N-methyl-3-aminomethyl-piperidine

This compound was prepared from 3-aminomethyl-pyridine by the method described in Biochem. J., 1971, 122, 557–567.

B) 2-chloro-5-(4-chlorophenyl)-1,3,4-thiadiazole

Preparation of this compound is described in U.S. Pat. No. 4,454,147.

Melting-point: 122° C.

C) SR 45 491 A

This compound is obtained from the products obtained in step A and step B, by the method described in the preceding Examples.

The hydrochloride is formed in the ethyl ether and 2-propanol solvent mixture.

Melting-point: 178° C.

Other compounds (I) according to the invention were prepared by methods of operation similar to those described hereinbefore. They are describe in Table 1 hereinafter and characterized by their melting point (Fc).

TABLE 1

$$R_1 \underset{N—N}{\overset{S}{\underset{\|}{\diagdown}}} \overset{R_2}{\underset{|}{N}}-R_3 \quad (I)$$

| N° Product | N° Example | $R_1$ | $R_3$ | Fc °C. (solvent) |
|---|---|---|---|---|
| SR 44824 A 2HCl | 12 | phenyl | 3-dimethyl-amino propyl | 230–232 EtOH |
| SR 45340 A 2HCl, H$_2$O | 13 | 5-bromo 2,4,6-tri-methyl-phenyl | 3-dimethyl-amino propyl | 218–220 EtOH |
| SR 45352 A 2HCl | 14 | 2,4,6-trimethyl phenyl | 3-diethyl-amino propyl | 188–190 EtOH |
| SR 45417 A 2HCl | 15 | 2,4,6-trimethyl phenyl | 3-pyridyl methyl | 190–192 EtOH |
| SR 45421 A 2HCl | 16 | 4-fluoro phenyl | 3-dimethyl-amino propyl | 233–235 iPrOH—Et$_2$O |
| SR 45422 A 2HCl | 17 | 2,4-dichloro phenyl | 3-dimethyl-amino propyl | 230–231 Et$_2$O |
| SR 45447 A | 18 | 4-fluoro phenyl | 3-pyridyl | 183–184 |
| SR 2HCl 0,5 H$_2$O | | phenyl | methyl | iPrOH—Et$_2$O |
| SR 45458 A 2HCl | 19 | 2,4-dichloro phenyl | 3-pyrrolidino propyl | 230 iPrOH |
| SR 45459 A 2HCl | 20 | 2,4-dichloro phenyl | 3-pyridyl methyl | 228 iPrOH |
| SR 45460 A HCl | 21 | 2,4-dichloro phenyl | 4-pyridyl methyl | 246 iPrOH |
| SR 45479 A 2HCl | 22 | 2,4-dichloro phenyl | 3-methyl-amino propyl | 237 iPrHO |
| SR 45480 A 2HCl | 23 | 4-chloro phenyl | 3-dimethyl-amino propyl | 238 iPrOH |
| SR 45481 A 2HCl | 24 | 2,4-dichloro phenyl | 3-diethyl-amino propyl | 122 iPrOH |
| SR 45482 A HCl | 25 | 4-fluoro phenyl | 4-pyridyl methyl | 222–224 iPrOH—Et$_2$O |
| SR 45483 A 2HCl 1,5 H$_2$O* | 26 | 4-fluoro phenyl | 3-dimethyl-amino propyl | 180–182 iPrOH—Et$_2$O |
| SR 45488 A | 27 | 4-chloro phenyl | 3-pyridyl methyl | 208 Et$_2$O |
| SR 45489 A 3 HCl | 28 | 4-chloro phenyl | 3-(4-methyl 1-piperazinyl) propyl | 256–257 iPrOH |
| SR 45490 A 2HCl 0,5 H$_2$O | 29 | 2,4-dichloro phenyl | 2-(1-methyl 2-pyrrolidinyl) ethyl | 228 iPrOH |
| SR 45492 A 2HCl | 30 | 2,4-dichloro phenyl | 2-(2-pyridyl) ethyl | 212 iPrOH |
| SR 45504 2HCl | 31 | 2,4-dichloro phenyl | 3-(1-imidazolyl) propyl | 258 iPrOH |
| SR 45520 A 2HCl, H$_2$O | 32 | 4-chloro phenyl | 3-morpholino propyl | 242 iPrOH |
| SR 45530 A 2HCl* | 33 | 4-fluoro phenyl | 3-pyridyl methyl | 254 iPrOH |
| SR 45544 A HCl 0,5 H$_2$O | 34 | 4-chloro phenyl | 4-pyridyl methyl | 244 iPrOH |
| SR 45640 A 2HCl | 35 | 4-tri-fluoro-methyl phenyl | 3-dimethyl-amino propyl | 220–222 EtOH |
| SR 45716 A 2HCl | 36 | 3-tri-fluoro-methyl phenyl | 3-dimethyl-amino propyl | 198–200 EtOH |
| SR 45717 2HCl | 37 | 2-chloro phenyl | 3-dimethyl-amino propyl | 244–246 EtOH |
| SR 45718 2HCl | 38 | 3-chloro phenyl | 3-dimethyl-amino propyl | 215–217 |

*The radical R$_2$ represents hydrogen except for the following compounds:
SR 45483 A where R$_2$ denotes ethyl and
SR 45530 A where R$_2$ denotes methyl The following abbreviations have been used for the recrystallization solvents: EtOH=ethanol, iPrOH=iso-propanol, Et$_2$O=ethyl ether.

The melting point (Fc) of certain compounds in base form was measured after they had been purified by chromatography:

| Example No | |
| --- | --- |
| 12 | Fc = 66-68° C. |
| 14 | Fc = 62-64° C. |
| 15 | Fc = 130-132° C. |
| 35 | Fc = 148-150° C. |
| 36 | Fc = 79-81° C. |
| 37 | Fc = 62-64° C. |
| 38 | Fc = 76-78° C. |

The products according to the invention were studied with regard to their pharmacological properties, more particularly their affinity for cholinergic muscarinic receptors.

They were studied by biochemical tests in vitro and also by pharmacological tests in the animal.

BIOCHEMICAL STUDY IN VITRO

Two sub-classes of cholinergic muscarinic receptors exist in mammals: receptors $M_1$ and $M_2$.

$M_1$ type receptors are concentrated in certain zones of the brain such as the hippocampus, the cerebral cortex, the corpus striatum and the sympathetic ganglia. These connection sites can be selectively tagged with tritiated pirenzepine ($^3$H—PZ). Type $M_2$ receptors predominate in the heart and the ileum and can be tagged with tritiated N-methylscopolamine ($^3$H—NMS). In order to determine the selectivity of the products according to the invention, with regard to sites $M_1$ and $M_2$, a study was made of their interaction in vitro, with high-affinity tagging with $^3$H—PZ and $^3$H—NMS, on rat hippocampus membranes and smooth muscle from guinea-pig ileum respectively.

Procedure a) Search for an affinity for the type $M_1$ muscarinic cholinergic receptor The interaction of molecules with type $M_1$ muscarinic receptors was studied in vitro on homogenized rat hippocampus, by studying the displacement of tritiated pirenzepine form its specific tagging sites. 10 µl portions of homogenized rat hippocampus (5% w/v) in an Na$_2$HPO$_4$ buffer (50 mM, pH 7.40) were incubated at 4° C. for 2 hours in the presence of $^3$H—Pz (76 Ci/mmol/1 nM final), with increasing concentrations of the product under study. The final volume was 2 ml. The reaction was stopped by centrifuging for 10 minutes at 50 000 g. After decantation and washing of the bottoms, the tagged radioactivity was counted by liquid scintillation. Non-specific tagging was determined in the presence of 10 µM of atropine sulphate.The 50 inhibiting concentration (IC$_{50}$) was determined graphically.

(Ref: J. D. Watson, W. R. Roeskoe and H. I. Yamamura, Life Sci., 1982, 31, 2019-2029).

b) Search for an affinity for the type $M_2$ muscarinic cholinergic receptor

Interaction with type $M_2$ muscarinic receptors was studies in vitro on homogenized smooth muscle of guinea-pig ileum by measuring the displacement of tritiated N-methyl-scopolamine from its specific tagging sites. 50 µl portions of homogenized smooth muscle form guinea-pig ileum (0.625% w/v) in 20 mM of HEPES buffer: 2-((2-hydroxy 4-ethyl) piperazin-1-yl) ethanesulphonic acid containing NaCl (100 mM) and Mg Cl$_2$ (10 mM) (final pH=7.5) were incubated at 30° C. for 20 minutes int eh presence of $^3$H—NMS (85 Ci/mmol/0.3 nM final) with increasing concentrations of the products under test. The final volume was 1 ml. The reaction was stopped by centrifuging for 5 minutes at 15000 g. Non-specific tagging was determined in the presence of 10 mM of atropine sulphate.

(Ref: R. Hammer et al., Nature, 1980, 283, 90-92; E. C. Hulme et al., Mol. Pharmacol., 1978, 14, 737-750).

Results

Table 2 shows the affinities of the products according to the invention for $M_1$ and $M_2$ receptors. The results are expressed as 50% inhibiting concentrations (IC$_{50}$), i.e. the concentration (in µM) which induces a 50% displacement of the tritiated ligand fixed to the membrane receptors. The IC$_{50}$ displacement of $^3$H—PZ represents affinity for the $M_1$ receptor, and The IC$_{50}$ displacement of $^3$H—NMS represents affinity for the $M_2$ receptor.

In the next column of the Table we show the ratio R between the IC$_{50}$ for receptors $M_1$ and $M_2$, which expresses the selectivity of the products relative to one type of receptor.

TABLE 2

| Product No. | $^3$H-PZ($M_1$) IC$_{50}$ µM | $^3$H-NMS($M_2$) IC$_{50}$ µM | $R = \dfrac{IC_{50}(M_2)}{IC_{50}(M_1)}$ |
| --- | --- | --- | --- |
| SR 44824 A | 3 | >100 | >30 |
| SR 44825 A | 2.5 | 80 | 32 |
| SR 44828 A | 9 | — | — |
| SR 45339 A | 5 | 34 | 7 |
| SR 45340 A | 3.5 | 27 | 6 |
| SR 45341 A | 0.45 | 72 | 160 |
| SR 45352 A | 5.5 | 30 | 5 |
| SR 45418 A | 20 | >100 | >5 |
| SR 45422 A | 0.70 | 26 | 37 |
| SR 45458 A | 0.8 | 12 | 15 |
| SR 45479 A | 14 | 70 | 5 |
| SR 45480 A | 4.5 | 50 | 11 |
| SR 45483 A | 2.4 | 20 | 8 |
| SR 45489 A | 3.6 | 26 | 7 |
| SR 45504 A | 3 | 40 | 13 |
| SR 45520 A | 4.5 | 80 | 17 |

The results show that the compounds according to the invention have strong affinity for muscarinic cholinergic receptors, with a marked specificity for type $M_1$ central receptors.

PHARMACOLOGICAL STUDY IN VIVO

Pirenzepine (PZ) is a specific antagonist of the $M_1$ central muscarinic cholinergic receptors. Intrastriatal injection of PZ into the mouse induces rotatory behaviour. Antagonism to this behaviour by the products according to the invention was studied.

The products according to the invention were administered in doses of 0.3 or 3 mg/kg orally after being solubilized in distilled water or suspended in a 5% solution of gum arabic. The controls were given pure solvent under the same conditions.

The animals used were female mice (Swiss, CD 1, Charles River, France), body weight between 25 and 30 grams.

Pirenzepine was dissolved in a phosphate buffer, the pH of the solution being 6.

The products under study or solvents thereof were orally administered, using a probang, in a volume of 0.4 ml per 20 g body weight. Administration occurred 4 hours before direct injection of pirenzepine, in a dose of 1 µg in 1 µl of solvent, into the right corpus striatum of the mouse, by the method described by P. WORMS at al in Psychopharmacology, 1987, 93, 489-492.

The number of contralateral rotations (in the opposite direction to the side of the injection) was counted for three 2-minute periods after injection of pirenzepine (minutes 2-4, 8-10 and 13-15) and was then totalled for each animal. Each treatment comprised three to four doses and ten animals per dose. For each treatment, the total number of rotations and the percentage inhibition relative to the control batch (solvent) was calculated.

The results are given in Table 3.

By way of comparison, results are given for certain products known in the prior art.

TABLE 3

| Product n° | % inhibition | |
|---|---|---|
| | 0,3 mg/kg p.o. | 3 mg/kg p.o. |
| SR 44824 A | −7 | −27** |
| SR 44828 A | −3 | −26** |
| SR 45339 A | −49** | −77** |
| SR 45340 A | −58** | −95** |
| SR 45341 A | −31** | −74** |
| SR 45352 A | −6 | −32** |
| SR 45417 A | −7 | −43** |
| SR 45418 A | −31** | −77** |
| SR 45421 A | −10 | −38** |
| SR 45422 | −7 | −50** |
| SR 45447 A | −36** | −62** |
| SR 45458 A | 0 | −28** |
| SR 45459 A | −11 | −29** |
| SR 45480 A | −35** | −54** |
| SR 45481 A | −31** | −67** |
| SR 45482 A | −23* | −53** |
| SR 45483 | 0 | −20* |
| SR 45488 A | −19 | −49** |
| SR 45489 A | 0 | −29** |
| SR 45490 A | −47** | −73** |
| SR 45491 A | −6 | −57** |
| SR 45492 A | −12 | −50** |
| SR A | −27* | −60** |
| SR 45520 A | −34** | −75** |
| SR 45530 A | −6 | −41** |
| A | −8 | −8 |
| B | Inactive | Inactive |
| C | −6 | −12 |

*p < 0.05 in Student's test
**p < 0.01 in Student's test.

Product A:

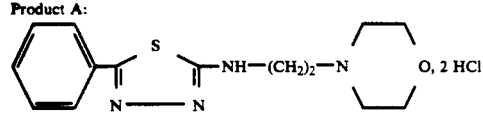

Product B:

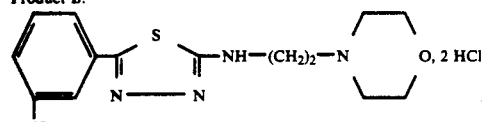

Product C:

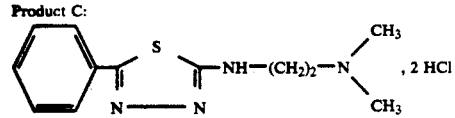

The results in table 3 show that the compounds according to the invention stimulate central cholinergic transmission and are therefore capable of use as agonists of the muscarinic receptors.

It has been found that the comparison products do not affect the central cholinergic transmission.

The products according to the invention do not show any sign of toxicity at the doses at which they are effective.

The acute toxicity was determined for one product according to the invention: SR 45341 A. The product was orally administered in increasing doses to a batch of 10 female mice (Swiss, CD 1, Charles River, France), body weight 20 g.

The death rate caused by the product under study was noted during the 24 hours after administration of the product. The 50% lethal dose ($DL_{50}$) was determined, i.e. the dose which killed 50% of the animals.

This dose was above 300 mg/kg.

Compounds (I) can therefore be used as drugs.

In view of the aforementioned results, the products according to the invention may be of use in the treatment of degenerative syndromes associated with ageing, inter alia disturbances of memory and senile dementia.

The invention therefore also relates to pharmaceutical compositions containing at least one of the formula (I) compounds or a salt thereof as the active ingredient.

In pharmaceutical compositions according to the invention for oral or sublingual or transdermic or rectal administration, the active ingredients of formula (I) hereinbefore can be administered in unit forms of administration, mixed with conventional pharmaceutical excipients. The appropriate unit forms of administration comprise oral forms, such as pills, capsules, powders, granulates and oral solutions or suspensions; sublingual and buccal forms, subcutaneous forms, intramuscular or intravenous forms and rectal forms.

In order to obtain the desired effect, the dose of active principle may vary between 20 and 500 mg per day. Each unit dose can contain 5 to 200 mg of active ingredient in combination with a pharmaceutical excipient. The unit dose can be administered 1 to 4 times per day.

when a solid composition is prepared in the form of pills, the main active ingredient is mixed with a pharmaceutical vehicle such as gelatine, starch, lactose, magnesium stearate, talcum, gum arabic or the like. Pills can be coated with saccharose or other suitable substances or can be treated to give them prolonged or delayed activity and so that they continuously release a given quantity of active principle.

A preparation in capsules can be obtained by mixing the active ingredient with a diluent and pouring the resulting mixture into soft or hard capsules.

Water-dispersible powders or granulates can contain the active ingredient mixed with dispersion agent or wetting agents or suspension agents such as polyvinyl pyrrolidone, or with sweeteners or taste adjusters.

Rectal administration is via suppositories prepared with binders melting at the rectal temperature, e.g. cocoa butter or polyethylene glycols.

Parenteral administration is via aqueous suspensions, isotonic saline solutions or sterile injectable solutions containing pharmacologically compatible dispersion agents and/or wetting agents, e.g. propylene glycol or butylene glycol.

Alternatively the active principle can be formulated in microcapsules, with one or more excipients or additives if required.

As an example of a galenic preparation, capsules containing

SR 45341 A: 0.010 g
Lactose: 0.050 g
Magnesium stearate: 0.005 g

We claim:
1. A thiadiazole derivative having the formula

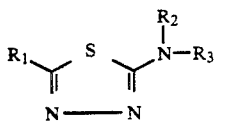

in which:
R₁ represents a phenyl group, non-substituted or substituted 1 to 3 times by any one of a halogen atom, a C₁-C₄ alkyl group, a C₁-C₄ alkoxy group, a hydroxy group or a trifluoromethyl group; or a phenyl group substituted simultaneously by 1 to 3 halogen atoms and by 1 or 2 methyl groups;
R₂ represents hydrogen or a C₁-C₄ alkyl group,
R₃ represents:

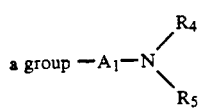

in which
A₁ denotes a straight chain C₃-C₄ alkyl group,
R₄ and R₅ considered independently represent hydrogen or a C₁-C₄ alkyl group, or R₄ or R₅ considered with the nitrogen atom bonded thereto constitute a 5- or 6-membered heterocyclic ring system containing one or two heteroatoms; or

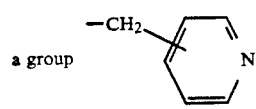

where the methylene group substitutes the pyridine ring in portions 3 or 4;

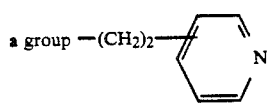

where the ethylene group substitutes the pyridine ring in position 2 or 3;

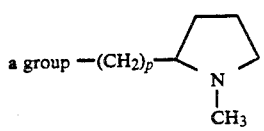

with p = 2 or 3;

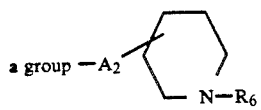

where R₆ denotes a methyl or ethyl group and A₂ denotes a (CH₂)$_m$ group where m=1 or 2, the A₂ group being in position 3 or 4 of the piperidine ring when m=1 and in position 2 or 3 thereof when m=2, or

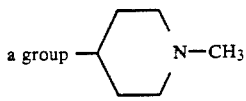

or alternatively the substituent

represents a group

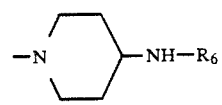

where R₆ is as indicated hereinbefore, or an addition salt thereof with a mineral or organic acid.

2. A compound according to claim 1, where R₃ represents:

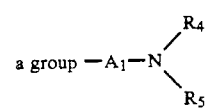

in which
A₁ denotes a C₃-C₄ straight-chain akyl group,
R₄ and R₃ considered independently represent hydrogen or a C₁-C₄ alkyl group, or R₄ and R₅ considered together with the nitrogen atom bonded thereto constitute a 5- or 6-membered heterocyclic ring system containing one or two heteroatoms.

3. A compound according to claim 1, where R₃ represents:

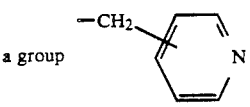

where the methylene group substitutes the pyridine ring in position 3 or 4.

4. A compound according to claim 1, where R₃ represents:

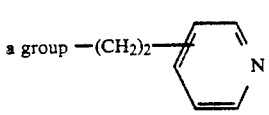

where the ethylene group substitutes the pyridine ring in position 2 or 3.

5. A compound according to claim 1, where R₃ represents:

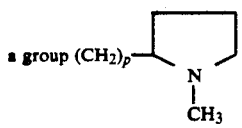

with p=2 or 3.

6. A compound according to claim 1, where R₃ represents:

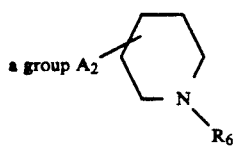

where
A₂ denotes a group (CH₂)$_m$ with m=1 or 2, and
R₆ denotes a methyl or ethyl group.

7. A compound according to claim 1, where R₃ represents:

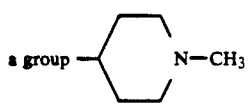

8. A compound according to claim 1, where R₃ represents:

represents a group:

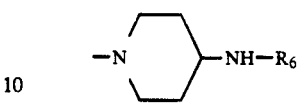

where R₆ denotes a methyl or ethyl group.

9. A thiadiazole derivative according to claim 1, wherein R₁ represents a phenyl group, substituted 1 to 3 times by at least one of chlorine and fluorine.

10. A thiadiazole derivative according to claim 1, wherein R₁ represents a phenyl group, substituted 1 to 3 times by a methyl group.

11. A thiadiazole derivative according to claim 1, wherein R₁ represents a phenyl group, substituted 1 to 3 times by a methoxy group.

12. A thiadiazole derivative according to claim 2, wherein the 5- or 6-membered heterocyclic ring system is selected from the group consisting of pyrrolidine, imidazole, piperidine, morpholine, piperazine and N-alkylpiperazine.

13. A pharmaceutical composition comprising an amount, effective for stimulating cholinergic transmission in a person suffering from memory disorder or senile dementia, of a thiadiazole derivative according to claim 1, and a pharmaceutically acceptable vehicle.

14. A pharmaceutical composition according to claim 13, wherein said amount of thiadiazole derivative is from 20 to 500 mg.

* * * * *